US008895501B2

(12) United States Patent
Eisenbach-Schwartz et al.

(10) Patent No.: US 8,895,501 B2
(45) Date of Patent: Nov. 25, 2014

(54) EYE-DROP VACCINE CONTAINING COPOLYMER 1 FOR THERAPEUTIC IMMUNIZATION

(75) Inventors: Michal Eisenbach-Schwartz, Rehovot (IL); Sharon Bakalash, Rehovot (IL); Valentin Fulga, Tel-Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 613 days.

(21) Appl. No.: 12/437,167

(22) Filed: May 7, 2009

(65) Prior Publication Data

US 2009/0214470 A1 Aug. 27, 2009

Related U.S. Application Data

(62) Division of application No. 10/541,492, filed as application No. PCT/IL2004/000006 on Jan. 6, 2004, now abandoned.

(60) Provisional application No. 60/438,310, filed on Jan. 7, 2003.

(51) Int. Cl.
| *A61K 38/00* | (2006.01) |
| *A61K 45/00* | (2006.01) |
| *A61K 38/20* | (2006.01) |
| *A61K 9/00* | (2006.01) |
| *A61K 39/00* | (2006.01) |
| *A61K 38/19* | (2006.01) |
| *A61K 38/02* | (2006.01) |
| *A61K 31/7088* | (2006.01) |
| *A61K 38/21* | (2006.01) |

(52) U.S. Cl.
CPC ......... *A61K 31/7088* (2013.01); *A61K 38/2013* (2013.01); *A61K 9/0048* (2013.01); *A61K 39/0008* (2013.01); *A61K 38/193* (2013.01); *A61K 38/02* (2013.01); *A61K 38/217* (2013.01); *A61K 38/208* (2013.01)
USPC .......................................... 514/2.1; 424/85.2

(58) Field of Classification Search
None
See application file for complete search history.

(56) References Cited

U.S. PATENT DOCUMENTS

| 5,571,515 | A | 11/1996 | Scott et al. |
| 6,214,791 | B1 | 4/2001 | Arnon et al. |
| 6,479,047 | B1 | 11/2002 | Lillard, Jr. |
| 6,844,314 | B2 | 1/2005 | Eisenbach-Schwartz et al. |
| 7,351,686 | B2 | 4/2008 | Eisenbach-Schwartz |
| 7,407,936 | B2 | 8/2008 | Eisenbach-Schwartz et al. |
| 2002/0037848 | A1 | 3/2002 | Eisenbach-Schwartz |
| 2011/0117115 | A1 | 5/2011 | Eisenbach-Schwartz |

FOREIGN PATENT DOCUMENTS

| JP | 4501562 | 3/1992 |
| JP | 7506565 | 7/1995 |
| JP | 2002510639 | 4/2002 |
| WO | 99/41247 A1 | 8/1999 |
| WO | 00/45847 A1 | 8/2000 |
| WO | 01/13896 A1 | 3/2001 |
| WO | 01/52878 A2 | 7/2001 |

OTHER PUBLICATIONS

Fulton et al (Avian Dis 44: 8-16, 2000).*
Chandler et al. Opthalmology 90: 585-591, 1983—abstract only.*
Seo et al. J Immunol 185: 3610-3619, 2010.*
Schori et al.,"Vaccination for protection of retinal ganglion cells against death from glutamate cytotoxicity and ocular hypertension: Implications for glaucoma", PNAS 98: 3398-3403 (2001).
Whitson.,"Glaucoma: a review of adjunctive therapy and new management strategies", Expert Opinion on Pharmacotherapy, 8:3237-3249 (2007).
Schori., et al., Vaccination for protection of retinal ganglion cells against death from glutamate cytotoxicity and ocular hypertension: Implications for glaucoma. Proceedings of the National Academy of Sciences of the United States of America, Mar. 13, 2001, vol. 98, No. 6, p. 3398-3403.
Kipnis. J, et al., T cell immunity to copolymer 1 confers neuroprotection on the damaged optic nerve: Possible therapy for optic neuropathies. Proceedings of the National Academy of Sciences of the United States of America, Jun. 20, 2000, vol. 97, No. 13, p. 7446-7451.
Teitalbaum, D., et al., Immunomodulation of experimental autoimmune encephalomyelitis by oral administration of copolymer 1, Proceedings of the National Academy of Sciences of the United States of America, Mar. 1999, vol. 96, p. 3842-3847.
"Intraocular" Merriam Webster Online Dictionary, Online [http://www.merriam-webster.com/dictionary/intraocular], dated Mar. 21, 2011.
"Ganciclovir (Intraocular Route)" Drugsfreelist.com, Online [http://www.drugsfreelist.com/leaflet_drug/4357935/Ganciclovir_Intraoc], dated Mar. 21, 2011.
"Ranibizumab (Intraocular Route)" Mayoclinic, Online [http://www.mayoclinic.com/health/drug-information/DR602403/DSECT], dated Mar. 21, 2011.
U.S. Appl. No. 10/582,163, filed Mar. 5, 2007.
"Intraocular" Stedman's Medical Dictionary, 26th Edition, p. 886 (1995).

* cited by examiner

*Primary Examiner* — Daniel E Kolker
*Assistant Examiner* — Aditi Dutt
(74) *Attorney, Agent, or Firm* — Browdy and Neimark, PLLC

(57) ABSTRACT

The invention provides an eye-drop vaccine for therapeutic immunization of a mammal comprising Copolymer 1, a Copolymer 1-related peptide, or a Copolymer 1-related polypeptide, for treating neuronal degeneration caused by an injury or disease, disorder or condition in the central nervous system (CNS) or peripheral nervous system (PNS), for preventing or inhibiting neuronal secondary degeneration which may otherwise follow primary injury in the CNS, for promoting nerve regeneration in the CNS or in the PNS after an injury, disease, disorder or condition or for protecting CNS and PNS cells from glutamate toxicity.

14 Claims, 5 Drawing Sheets

SEQUENCE LISTING

```
<160> NUMBER OF SEQ ID NOS: 32

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Ala Ala Ala Tyr Ala Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Ala Glu Lys Tyr Ala Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide

<400> SEQUENCE: 3

Ala Lys Glu Tyr Ala Ala Ala Ala Ala Lys Ala Ala Ala Ala
1               5                   10                  15
```

```
<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Ala Lys Lys Tyr Ala Ala Ala Ala Ala Lys Ala Ala Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Ala Glu Ala Tyr Ala Ala Ala Ala Ala Lys Ala Ala Ala Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Lys Glu Ala Tyr Ala Ala Ala Ala Ala Lys Ala Ala Ala Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Ala Glu Glu Tyr Ala Ala Ala Ala Ala Lys Ala Ala Ala Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Ala Ala Glu Tyr Ala Ala Ala Ala Ala Lys Ala Ala Ala Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Glu Lys Ala Tyr Ala Ala Ala Ala Ala Lys Ala Ala Ala Ala Ala
1               5                   10                  15

<210> SEQ ID NO 10
```

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Ala Ala Lys Tyr Glu Ala Ala Ala Lys Ala Ala Ala Ala
1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Ala Ala Lys Tyr Ala Glu Ala Ala Ala Lys Ala Ala Ala Ala
1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Glu Ala Ala Tyr Ala Ala Ala Ala Ala Lys Ala Ala Ala Ala
1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Glu Lys Lys Tyr Ala Ala Ala Ala Ala Lys Ala Ala Ala Ala
1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Glu Ala Lys Tyr Ala Ala Ala Ala Ala Lys Ala Ala Ala Ala
1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Ala Glu Lys Tyr Ala Ala Ala Ala Ala Ala Ala Ala Ala Ala
1               5                  10                  15

<210> SEQ ID NO 16
<211> LENGTH: 15
```

```
<212> TYPE: PRT
<213> ORGANISM: Artificial Sequence
<220> FEATURE:
<223> OTHER INFORMATION: Synthetic peptide

<400> SEQUENCE: 16

Ala Lys Glu Tyr Ala Ala Ala Ala Ala Ala Ala Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Ala Lys Lys Tyr Glu Ala Ala Ala Ala Ala Ala Ala Ala
1               5                   10                  15

<210> SEQ ID NO 18
<211> LENGTH: 15
<212> TYPE: PRT
<213> ORGANISM: Artificial Sequenece
<220> FEATURE:
<223> OTHER INFORMATION: Synthetic peptide

<400> SEQUENCE: 18

Ala Lys Lys Tyr Ala Glu Ala Ala Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Ala Glu Ala Tyr Lys Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Lys Glu Ala Tyr Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Ala Glu Glu Tyr Lys Ala Ala Ala Ala Ala Ala Ala Ala
1               5                   10                  15

<210> SEQ ID NO 22
<211> LENGTH: 15
<212> TYPE: PRT
```

```
<213> ORGANISM: Artificial Sequence
<220> FEATURE:
<223> OTHER INFORMATION: Synthetic peptide

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 28

Ala Glu Tyr Ala Lys Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

Ala Glu Lys Ala Tyr Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Glu Lys Tyr Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

Ala Tyr Lys Ala Glu Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

Ala Lys Tyr Ala Glu Ala Ala Ala Ala Ala Ala Ala Ala Ala
1               5                   10                  15
```

EYE-DROP VACCINE CONTAINING COPOLYMER 1 FOR THERAPEUTIC IMMUNIZATION

FIELD OF THE INVENTION

The present invention is in the field of Immunology and relates to an eye-drop vaccine comprising a random copolymer, in particular Copolymer 1, a Copolymer 1-related peptide, or a Copolymer 1-related polypeptide, as the active agent, and to a method of therapeutic immunization of a mammal, in particular for neuroprotection in the central nervous system (CNS) or in the peripheral nervous system (PNS) after an injury, disease, disorder or condition or for protecting CNS and PNS cells from glutamate toxicity.

Abbreviations:

BSA: bovine serum albumin; CFA: complete Freund's adjuvant; CNS: central nervous system; Cop 1: Copolymer 1, glatiramer acetate; FCS: fetal calf serum; IFA: incomplete Freund's adjuvant; IOP: intraocular pressure; MBP: myelin basic protein; NS: nervous system; PBS: phosphate-buffered saline; PNS: peripheral nervous system; RGC: retinal ganglion cells.

BACKGROUND OF THE INVENTION

The nervous system comprises the central and the peripheral nervous system. The peripheral nervous system (CNS) is composed of the brain and spinal cord; the peripheral nervous system (PNS) consists of all of the other neural elements, namely the nerves and ganglia outside of the brain and spinal cord.

Damage to the nervous system may result from a traumatic injury, such as penetrating trauma or blunt trauma, or a disease, disorder or condition, including but not limited to Alzheimer's disease, Parkinson's disease, Huntington's disease, amyotrophic lateral sclerosis, diabetic neuropathy, glaucoma, senile dementia, and ischemia.

Neurodegenerative disorders are commonly associated with ongoing neuronal loss in the CNS. Following the loss of neurons caused by primary risk factors, additional ("secondary") neuronal loss is mediated by self-compounds, such as glutamate, nitric oxide or reactive oxygen species, that exceed their physiological concentrations. These compounds are implicated in various types of neurological disorders and acute CNS injuries. It is interesting to note that the destructive components common to neurodegenerative diseases have also been identified in autoimmune diseases such as multiple sclerosis; in this disease, myelin damage in the CNS is accompanied by subsequent neuronal loss.

Glaucoma is a slow-progressing optic neuropathy with a high incidence in the elderly population (approximately 1%). Until recently, it was associated with high intraocular pressure (IOP) and therefore attempts have been focused on slowing down the disease progression by anti-hypertensive drugs. Over the years, it became apparent that glaucoma is a family of diseases and not all are associated with pressure. Moreover, it became clear that even when the disease is associated with pressure, the latter may be reduced to normal and even below normal values and degeneration may continue. An ongoing discussion among clinicians has questioned whether the continuous degeneration in glaucomatous patients, in spite of normal IOP values, is a reflection of the existence of additional risk factors besides pressure or a reflection of the increased vulnerability of the remaining neurons and fibers and thus the need to reduce IOP below normal values.

We have suggested in 1996 that the mechanism underlying progressive loss of vision in glaucoma is similar to that occurring in any acute insult to the nervous system or any neurodegenerative disease of the CNS (Schwartz et al, 1996). According to this proposal, in addition to the primary risk factor, e.g. pressure, there is an ongoing process of degeneration that affects neurons that spared the primary event (Schwartz et al, 1996; Schwartz and Yoles, 2000a and 2000b). This process is mediated by compounds that emerged as a result of the primary event or by deficit as a result of the primary risk factor, all of which create a hostile environment to neurons adjacent to the primary insult.

We have further recently observed that under neurodegenerative conditions caused by mechanical (axotomy) or biochemical (glutamate, oxidative stress) insults, the immune system plays a critical role. Thus, it has been found that activated T cells that recognize an antigen of the nervous system (NS) promote nerve regeneration or confer neuroprotection, as described for example in PCT Publication No. WO 99/60021. More specifically, T cells reactive to myelin basic protein (MBP) were shown to be neuroprotective in rat models of partially crushed optic nerve (Moalem et al., 1999) and of spinal cord injury (Hauben et al., 2000). Until recently, it had been thought that the immune system excluded immune cells from participating in nervous system repair. It was quite surprising to discover that NS-specific activated T cells could be used to promote nerve regeneration or to protect nervous system tissue from secondary degeneration which may follow damage caused by injury or disease of the CNS or PNS.

It was further observed by the present inventors that stressful conditions in the CNS harness the adaptive immune response to cope with the stress and that this response is genetically controlled. Thus, the survival rate of retinal ganglion cells (RGCs) in adult mice or rats after crush injury of the optic nerve or intravitreal injection of a toxic dosage of glutamate was shown to be up to two-fold higher in strains that are resistant to CNS autoimmune diseases than in susceptible strains. The difference was found to be attributable to a beneficial autoimmune T cell response that was spontaneously evoked after CNS insult in the resistant, but not in susceptible, strains. Thus, the survival rate of neurons as a result of such an insult is higher when T cell response directed against self is evoked, provided that it is well-regulated. In other words, it was demonstrated that a protective autoimmune response is evoked to oppose the stressful conditions so as to protect the animal from the insult consequences. It was further observed that in animals with an impaired ability to regulate such a response, or in animals devoid of mature T cells (as a result of having undergone thymectomy at birth), the ability to cope with the stressful conditions is reduced. Consequently, the survival rate of neurons following CNS insult in these animals is significantly lower than in animals endowed with an effective mechanism for mounting protective autoimmune T cell-mediated response (Kipnis et al., 2001).

More recent studies in our laboratory have shown that autoimmune neuroprotection is the body's physiological defense mechanism awakened when CNS injury occurs (Kipnis et al., 2001; Yoles et al., 2001). We demonstrated that resistance to increased IOP differs among strains (Bakalash et al., 2002) and that this difference is linked to the ability to harness an autoimmune response with a beneficial outcome. We further showed that in the absence of mature T cells (through neonatal thymectomy), the relative resistance to IOP elevation loses its beneficial trait, and vice versa, when splenocytes from a resistant strain are passively transferred to an MHC-matched susceptible strain, the neuroprotective effect is resumed (Bakalash et al., 2002). It was further shown by our group that passive vaccination with T cells is also effective in acute injuries such as partial optic nerve crush or spinal cord contusion (Kipnis et al., 2001; Moalem et al., 1999).

Attempting to boost such an anti-self response as a way of protecting neurons from insulting conditions has revealed that the vaccinating antigen should be derived from compounds residing in the site of the lesion. Thus, the use of the self-antigen derived from interphotoreceptor binding protein (IRBP), the most abundant peptide in the eye (Bakalash et al., 2002; Mizrahi et al., 2002), resulted in RGC protection in both susceptible and resistant strains. In contrast, the use of peptides derived from compounds residing in the myelin associated with the optic nerve led to no benefit to the retinal ganglion cells suffering from IOP elevated insult.

Trying to design a vaccination for glaucoma that will boost the immune system without risk of evoking an autoimmune disease, we chose to focus on Copolymer 1, and have shown that it is neuroprotective for glaucoma when given with an adjuvant (Bakalash et al., 2002; Schori et al., 2001; Schwartz and Kipnis, 2002; WO 01/52878; WO 01/93893). Cop-1 immunologically cross-reacts with a wide variety of self-reactive T cells. Accordingly, its activity is reminiscent of that of altered peptide ligand, a self-peptide that has been altered and has lost pathogenicity as a result (WO 02/055010; Kipnis and Schwartz, 2002).

Copolymer 1, also called Cop 1 or glatiramer acetate, is a non-pathogenic synthetic random copolymer composed of the four amino acids: L-Glu, L-Lys, L-Ala, and L-Tyr, with an average molecular fraction of 0.141, 0.338, 0.427, and 0.095, respectively, and an average molecular weight of 4,700-11,000. COPAXONE® (a trademark of Teva Pharmaceutical Industries Ltd., Petach Tikva, Israel), the brand name for glatiramer acetate, is currently an approved drug in many countries for the treatment of multiple sclerosis. It is very well tolerated with only minor adversary reactions. Although treatment with Cop 1 by ingestion or inhalation is disclosed in U.S. Pat. No. 6,214,791, the sole route of administration of Cop 1 to multiple sclerosis patients is by daily subcutaneous injection.

Recently it was found that in animal models Cop 1 provides a beneficial effect for several additional disorders. Thus, Cop 1 suppresses the immune rejection manifested in graft-versus-host disease (GVHD) in case of bone marrow transplantation (Schlegel et al., 1996; U.S. Pat. No. 5,858,964), as well as in graft rejection in case of solid organ transplantation (Aharoni et al., 2001). Cop 1 and Cop 1-related copolymers and peptides have been disclosed in WO 00/05250 for treating autoimmune diseases.

WO 01/52878 and WO 01/93893 of the present applicants disclose that Cop 1, Cop 1-related peptides and polypeptides and T cells activated therewith protect CNS cells from glutamate toxicity and prevent or inhibit neuronal degeneration or promote nerve regeneration in the CNS and PNS. WO 01/93828 discloses that Cop 1 can be used for treatment of CNS disorders. None of these publications discloses immunization by administration of eye-drops containing Cop 1.

Poultry vaccines for administration as eye drops comprising a live virus or recombinant DNA coding for immunogenic proteins from infectious agents have been described for prevention of viral diseases in avian animals (Mukibi-Muka et al., 1984; Sharma, 1999; Russell and Mackie, 2001).

Citation or identification of any reference in this section or any other part of this application shall not be construed as an admission that such reference is available as prior art to the invention.

SUMMARY OF THE INVENTION

It has now been found, in accordance with the present invention, that Copolymer 1, when administered as an eye-drop vaccine, evokes a systemic T cell-dependent immune response needed for neuroprotection in the CNS or PNS, as exemplified by protection of retinal ganglion cells (RGCs) against death induced by acute or chronic intraocular pressure (IOP) elevation.

The present invention thus relates, in one aspect, to an eye-drop vaccine comprising an active agent selected from the group consisting of Copolymer 1, a Copolymer 1 related-peptide, and a Copolymer 1-related polypeptide.

In another aspect, the present invention relates to the use of an active agent selected from the group consisting of Copolymer 1, a Copolymer 1 related-peptide, and a Copolymer 1-related polypeptide, for the manufacture of an eye-drop vaccine.

The eye-drop vaccine according to the invention is particularly useful for therapeutic immunization of a mammal, in particular humans, for neuroprotection for treating neuronal degeneration caused by an injury, disease, disorder or condition in the central nervous system (CNS) or peripheral nervous system (PNS), for preventing or inhibiting neuronal secondary degeneration which may otherwise follow a primary injury in the CNS, for promoting nerve regeneration in the CNS or in the PNS after an injury, disease, disorder or condition, or for protecting CNS and PNS cells from glutamate toxicity.

In a further aspect, the present invention provides a method of therapeutic immunization for treating neuronal degeneration caused by an injury, disease, disorder or condition in the central nervous system (CNS) or peripheral nervous system (PNS), for preventing or inhibiting neuronal secondary degeneration which may otherwise follow a primary injury in the CNS, for promoting nerve regeneration in the CNS or in the PNS after an injury, disease, disorder or condition or for protecting CNS and PNS cells from glutamate toxicity, which comprises immunizing an individual in need with an eye-drop vaccine comprising an active agent selected from the group consisting of Copolymer 1, a Copolymer 1-related peptide, and a Copolymer 1-related polypeptide, in an amount effective to treat, prevent or inhibit said neuronal degeneration caused by said injury, disease, disorder or condition in the individual.

In the eye-drop vaccine of the invention, the active agent may be administered without any adjuvant, for example in saline or phosphate-buffered saline (PBS), or it may be administered with a soluble adjuvant such as a cytokine, e.g. IL-2, IL-12, GM-CSF or IFN-γ, and the like.

In the most preferred embodiment, the active agent of the eye-drop vaccine of the invention is Copolymer 1.

DETAILED DESCRIPTION OF THE INVENTION

Figure 1:
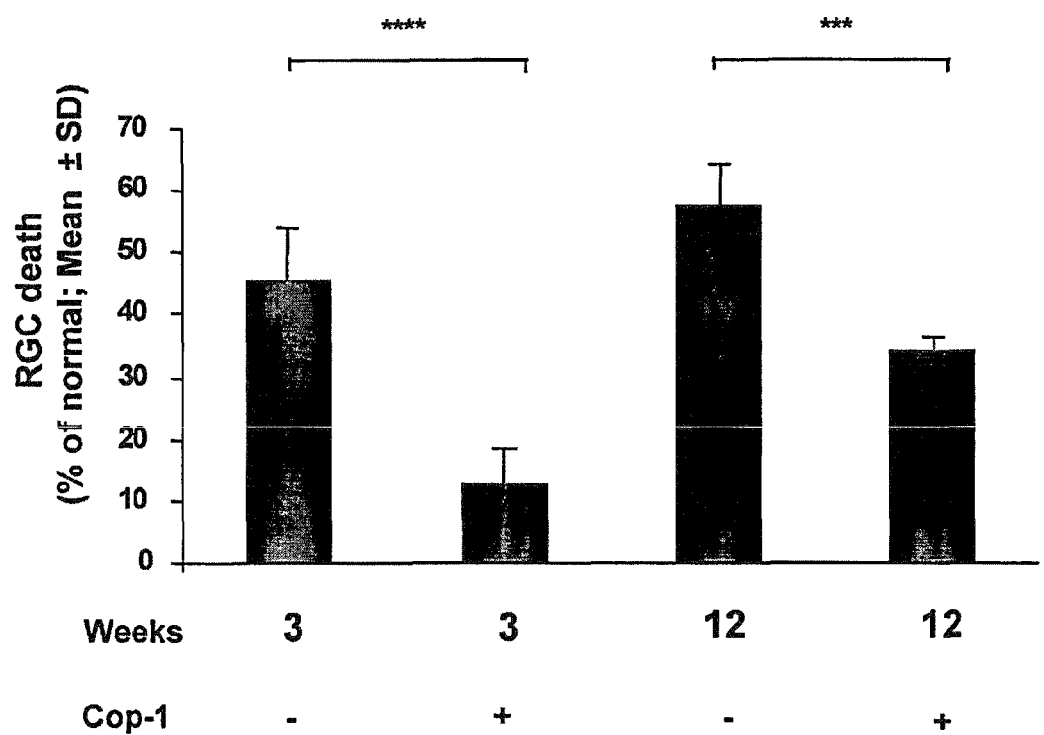
FIG. 1 shows that Copolymer 1 (Cop-1) has a long-lasting effect in protecting RGCs from IOP-induced death in a chronic model.

As used herein, the terms "Copolymer 1", "Cop 1", "Cop-1", and "glatiramer acetate" are each used interchangeably.

For the purpose of the present invention, "Cop 1 or a Cop 1-related peptide or polypeptide" is intended to include any peptide or polypeptide, including a random copolymer, that cross-reacts functionally with myelin basic protein (MBP) and is able to compete with MBP on the MHC class II in the antigen presentation.

A copolymer for use as active agent in the eye-drop vaccine of the present invention may be a random copolymer comprising a suitable quantity of a positively charged amino acid such as lysine (K) or arginine (R), in combination with a negatively charged amino acid (preferably in a lesser quantity) such as glutamic acid (E) or aspartic acid (D), optionally in combination with a non-charged neutral amino acid such as alanine (A) or glycine (G), serving as a filler, and optionally with an amino acid adapted to confer on the copolymer immunogenic properties, such as an aromatic amino acid like tyrosine (Y) or tryptophan (W).

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the copolymers used in the present invention. The present invention contemplates the use of copolymers containing both D- and L-amino acids, as well as copolymers consisting essentially of either L- or D-amino acids.

In one embodiment, the active agent for use in the present invention comprises at least one random three- or four-amino acid copolymer comprising one amino acid selected from each of the four following groups: (a) lysine (K) and arginine (R); (b) glutamic acid (E) and aspartic acid (D); (c) alanine (A) and glycine (G); and (d) tyrosine (Y) and tryptophan (W).

In one preferred embodiment, the copolymer comprises a combination of the amino acids tyrosine, glutamic acid, alanine, and lysine, herein designated poly-YEAK, of net overall positive electrical charge, and is most preferably Copolymer 1, of the following molar ratio of the amino acids: about 0.14 glutamic acid, about 0.43 alanine, about 0.10 tyrosine, and about 0.34 lysine. It may be a low molecular weight or high molecular weight copolymer being a polypeptide from about 15 to about 100, preferably from about 40 to about 80, amino acids in length. The copolymer has an average molecular weight of about 2,000-40,000 Da, preferably of about 2,000-13,000 Da, more preferably of about 4,700-13,000 Da, most preferably of about 5,000-9,000 Da, and mostly preferred of about 6,000-8,000 Da. This preferred copolymer, Cop 1, is most preferably in the form of its acetate salt known under the generic name glatiramer acetate. Preferred molecular weight ranges and processes for making a preferred form of Cop 1 are described in U.S. Pat. No. 5,800,808, the entire contents of which are hereby incorporated by reference in their entirety as if fully disclosed herein.

It is clear that this is given by way of example only, and that the active agent can be varied both with respect to the constituents and relative proportions of the constituents, thus obtaining poly-YEAK copolymers different from Cop 1.

In another embodiment, the active agent of the eye-drop vaccine of the invention is a Cop 1-related polypeptide that is a random copolymer containing four different amino acids, each from a different one of the groups (a) to (d), but excluding Cop 1. The activity exhibited by Copolymer 1 is expected to remain if one or more of the following substitutions is made in the amino acid composition of the copolymer: aspartic (D) acid for glutamic acid (E), glycine (G) for alanine (A), arginine (R) for lysine (K), and tryptophan (W) for tyrosine (Y).

Thus, in another embodiment, the Cop 1-related polypeptide of the invention may include any of those copolymers disclosed in WO 00/05250, the entire contents of which being hereby incorporated herein by reference as if fully disclosed herein, and other synthetic amino acid copolymers such as the random four-amino acid copolymers described by Fridkis-Hareli et al. (2002) as candidates for treatment of multiple sclerosis, namely copolymers (14-, 35- and 50-mers) containing the amino acids phenylalanine, glutamic acid, alanine and lysine (poly-FEAK), or tyrosine, phenylalanine, alanine and lysine (poly-YFAK), and any other similar copolymer to be discovered that can be considered a universal antigen similar to Cop 1.

In another embodiment, the Cop 1-related polypeptide of the invention is a copolymer containing a combination of three different amino acids each from a different one of three groups of the groups (a) to (d). These copolymers are herein referred to as terpolymers. In a more preferred embodiment, the mole fraction of amino acids of the terpolymers is about what is preferred for Copolymer 1.

In one embodiment, the terpolymers for use in the present invention contain tyrosine (Y), alanine (A), and lysine (K), hereinafter designated poly-YAK. The average molar fraction of the amino acids in these terpolymers can vary. For example, tyrosine can be present in a mole fraction of about 0.005-0.250; alanine can be present in a mole fraction of about 0.3-0.6; and lysine can be present in a mole fraction of about 0.1-0.5, but preferably the molar ratios of tyrosine, alanine and lysine are about 0.10 to about 0.54 to about 0.35. The average molecular weight of poly-YAK is about 2,000-40,000 Da, preferably about 3,000-35,000 Da, more preferably about 5,000-25,000 Da. It is possible to substitute arginine (R) for lysine (K), glycine (G) for alanine (A), and/or tryptophan (W) for tyrosine (Y).

In another embodiment, the terpolymers for use in the present invention contain tyrosine (Y), glutamic acid (E), and lysine (K), hereinafter designated poly-YEK. The average mole fraction of the amino acids in these terpolymers can vary: glutamic acid can be present in a mole fraction of about 0.005-0.300, tyrosine can be present in a mole fraction of about 0.005-0.250, and lysine can be present in a mole fraction of about 0.3-0.7, but preferably the molar ratios of glutamic acid, tyrosine, and lysine are about 0.26 to about 0.16 to about 0.58. The average molecular weight of poly-YEK is about 2,000-40,000 Da, preferably about 3,000-35,000 Da, more preferably about 5,000-25,000 Da. It is possible to substitute arginine (R) for lysine (K), aspartic acid (D) for glutamic acid (E), and/or tryptophan (W) for tyrosine (Y).

In a further embodiment, the terpolymers for use in the present invention contain lysine (K), glutamic acid (E), and alanine (A), hereinafter designated poly-KEA. The average molar fraction of the amino acids in these polypeptides can also vary. For example, glutamic acid can be present in a mole fraction of about 0.005-0.300, alanine in a mole fraction of about 0.005-0.600, and lysine can be present in a mole fraction of about 0.2-0.7, but preferably the molar ratios of glutamic acid, alanine and lysine are about 0.15 to about 0.48 to about 0.36. The average molecular weight of YEK is about 2,000-40,000 Da, preferably about 3,000-35,000 Da, more preferably about 5,000-25,000 Da. It is possible to substitute arginine (R) for lysine (K), aspartic acid (D) for glutamic acid (E), and/or glycine (G) for alanine (A).

In still another embodiment, the terpolymers for use in the present invention contain tyrosine (Y), glutamic acid (E), and alanine (A), hereinafter designated poly-YEA. The average molar fraction of the amino acids in these polypeptides can vary. For example, tyrosine can be present in a mole fraction of about 0.005-0.250, glutamic acid can be present in a mole fraction of about 0.005-0.300, and alanine can be present in a mole fraction of about 0.005-0.800, but preferably the molar ratios of glutamic acid, alanine, and tyrosine are about 0.21 to about 0.65 to about 0.14. The average molecular weight of poly-YEA is about 2,000-40,000 Da, preferably about 3,000-35,000 Da, and more preferably about 5,000-25,000 Da. It is possible to substitute tryptophan (W) for tyrosine (Y), aspartic acid (D) for glutamic acid (E), and/or glycine (G) for alanine (A).

The terpolymers can be made by any procedure available to one of skill in the art, for example as described in the above-mentioned publications WO 01/52878 and WO 01/93893.

As binding motifs of Cop 1 to MS-associated HLA-DR molecules are known, polypeptides of fixed sequence can readily be prepared and tested for binding to the peptide-binding groove of the HLA-DR molecules as described in Fridkis-Hareli et al. (1999). Examples of such peptides are those disclosed in WO 005249, the entire contents of which are hereby incorporated by reference as if fully disclosed herein. Thirty-two of the peptides specifically disclosed in said application are reproduced in Table I hereinbelow (SEQ ID NO: 1 to NO:32). These are 15-mer peptides comprising the 4 amino acids alanine, glutamic acid, lysine and tyrosine (peptides 2, 3, 5-32) or only the 3 amino acids alanine, lysine and tyrosine (peptides 1, 4). Such peptides and other similar peptides would be expected to have similar activity as Cop 1 and are encompassed within the definition of Cop 1-related peptides or polypeptides of the invention.

TABLE 1

| SEQ ID NO. | Peptide Sequence |
|---|---|
| 1 | AAAYAAAAAAKAAAA |
| 2 | AEKYAAAAAAKAAAA |
| 3 | AKEYAAAAAAKAAAA |
| 4 | AKKYAAAAAAKAAAA |
| 5 | AEAYAAAAAAKAAAA |
| 6 | KEAYAAAAAAKAAAA |
| 7 | AEEYAAAAAAKAAAA |
| 8 | AAEYAAAAAAKAAAA |
| 9 | EKAYAAAAAAKAAAA |
| 10 | AAKYAAAAAAKAAAA |
| 11 | AAKYAEAAAAAKAAAA |
| 12 | EAAYAAAAAAKAAAA |

TABLE 1-continued

| SEQ ID NO. | Peptide Sequence |
|---|---|
| 13 | EKKYAAAAAAKAAAA |
| 14 | EAKYAAAAAAKAAAA |
| 15 | AEKYAAAAAAAAAAA |
| 16 | AKEYAAAAAAAAAAA |
| 17 | AKKYEAAAAAAAAAA |
| 18 | AKKYAEAAAAAAAAA |
| 19 | AEAYKAAAAAAAAAA |
| 20 | KEAYAAAAAAAAAAA |
| 21 | AEEYKAAAAAAAAAA |
| 22 | AAEYKAAAAAAAAAA |
| 23 | EKAYAAAAAAAAAAA |
| 24 | AAKYEAAAAAAAAAA |
| 25 | AAKYAEAAAAAAAAA |
| 26 | EKKYAAAAAAAAAAA |
| 27 | EAKYAAAAAAAAAAA |
| 28 | AEYAKAAAAAAAAAA |
| 29 | AEKAYAAAAAAAAAA |
| 30 | EKYAAAAAAAAAAAA |
| 31 | AYKAEAAAAAAAAAA |
| 32 | AKYAEAAAAAAAAAA |

The present invention relates, in one aspect, to an eye-drop vaccine comprising an active agent selected from the group consisting of Copolymer 1, a Copolymer 1 related-peptide, and a Copolymer 1-related polypeptide.

In another aspect, the present invention relates to the use of an active agent selected from the group consisting of Copolymer 1, a Copolymer 1 related-peptide, and a Copolymer 1-related polypeptide for the manufacture of an eye-drop vaccine.

In one embodiment, the eye-drop vaccine comprises the active agent dissolved in any suitable carrier such as saline or PBS, without any adjuvant.

In another embodiment, the eye-drop vaccine comprises the active agent together with a suitable soluble adjuvant such as a soluble cytokine as exemplified, but not limited to, the cytokines IL-2, IL-12, GM-CSF or IFN-γ.

The present invention further relates to a method of therapeutic immunization for neuroprotection which comprises immunizing an individual in need with an eye-drop vaccine comprising an active agent selected from the group consisting of Copolymer 1, a Copolymer 1 related-peptide, and a Copolymer 1-related polypeptide, in an amount effective to afford neuroprotection to said individual.

In one embodiment, the invention provides a method of therapeutic immunization for treating neuronal degeneration caused by an injury in the CNS or PNS, which comprises immunizing an individual in need with an eye-drop vaccine comprising an active agent selected from the group consisting of Copolymer 1, a Copolymer 1 related-peptide, and a Copolymer 1-related polypeptide, in an amount effective to treat the neuronal degeneration caused by the injury in said individual.

In another embodiment, the invention provides a method of therapeutic immunization for preventing or inhibiting neuronal secondary degeneration which may otherwise follow a primary injury in the CNS, which comprises immunizing an individual in need with an eye-drop vaccine comprising an active agent selected from the group consisting of Copolymer 1, a Copolymer 1 related-peptide, and a Copolymer 1-related polypeptide, in an amount effective for preventing or inhibiting the neuronal degeneration which may follow a primary injury in the CNS of said individual.

In a further embodiment, the invention provides a method of therapeutic immunization for promoting nerve regeneration in the CNS or in the PNS after an injury, which comprises immunizing an individual in need with an eye-drop vaccine comprising an active agent selected from the group consisting of Copolymer 1, a Copolymer 1 related-peptide, and a Copolymer 1-related polypeptide, in an amount effective for promoting nerve regeneration in the CNS or in the PNS of said individual after the injury.

Any injury in the CNS or PNS can be treated according to the invention such as, but not limited to, spinal cord injury, blunt trauma, penetrating trauma, brain coup or contrecoup, hemorrhagic stroke, and ischemic stroke.

In yet another embodiment, the invention relates to a method of therapeutic immunization for treating neuronal degeneration caused by a disease, disorder or condition in the CNS or PNS, which comprises immunizing an individual in need with an eye-drop vaccine comprising an active agent selected from the group consisting of Copolymer 1, a Copolymer 1 related-peptide, and a Copolymer 1-related polypeptide, in an amount effective to treat the neuronal degeneration caused by the disease, disorder or condition in the CNS or PNS of said individual.

In yet a further embodiment, the invention relates to a method of therapeutic immunization for promoting nerve regeneration in the CNS or in the PNS after a disease, disorder or condition, which comprises immunizing an individual in need with an eye-drop vaccine comprising an active agent selected from the group consisting of Copolymer 1, a Copolymer 1 related-peptide, and a Copolymer 1-related polypeptide, in an amount effective to promote nerve regeneration in the CNS or in the PNS needed following a disease, disorder or condition of the CNS or PNS in said individual.

In still a further embodiment, the invention relates to a method of therapeutic immunization for protecting CNS and PNS cells from glutamate toxicity, which comprises immunizing an individual in need with an eye-drop vaccine comprising an active agent selected from the group consisting of Copolymer 1, a Copolymer 1 related-peptide, and a Copolymer 1-related polypeptide, in an amount effective to protect CNS or PNS cells in said individual from glutamate toxicity.

Among the diseases, disorders and conditions that may be treated according to the invention are, without being limited to, a senile dementia including Alzheimer's disease, a Parkinsonian syndrome including Parkinson's disease, facial nerve (Bell's) palsy, Huntington's chorea, a motor neuron disease including amyotrophic lateral sclerosis, a prion disease including Creutzfeldt-Jakob disease, Alper's disease, Batten disease, Cockayne syndrome, Lewy body disease, status epilepticus, carpal tunnel syndrome, intervertebral disc herniation, vitamin deficiency such as vitamin B deficiency, epilepsy, amnesia, anxiety, hyperalgesia, psychosis, seizures, oxidative stress, opiate tolerance and dependence, an autoimmune disease such as multiple sclerosis (MS), or a peripheral neuropathy associated with a disease such as amyloid polyneuropathy, diabetic neuropathy, uremic neuropathy, porphyric polyneuropathy, hypoglycemia, Sjogren-Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs such as nitrofurantoin, metronidazole, isoniazid and toxins such as alcohol or organophosphates, Charcot-Marie-Tooth disease, ataxia telangiectasia, Friedreich's ataxia, adrenomyeloneuropathy, giant axonal neuropathy, Refsum's disease, Fabry's disease, lipoproteinemia, non-arteritic optic neuropathy, age-related macular degeneration, a retinal disorder such as retinal degeneration or a disease associated with abnormally elevated intraocular pressure such as glaucoma.

As mentioned in the Background of the Invention section, we have suggested in 1996 that perhaps in glaucoma, like in any acute insult to the nervous system or any neurodegenerative disease of the CNS, there is an ongoing process of degeneration that affects neurons that spared the primary event, e.g. pressure elevation (Schwartz et al, 1996). This process is mediated by compounds that emerged as a result of the primary event or by deficit as a result of the primary risk factor, all of which create a hostile environment to neurons adjacent to the primary insult (Schwartz et al, 1996; Schwartz and Yoles, 2000a and 2000b). Recognition that such processes may take place in glaucoma, encouraged us to search for a therapy that, if given at any time, it may stop the progression of degeneration.

Indeed, since 1996 attempts are being made worldwide to identify mediators of toxicity to find ways that block, circumvent or eliminate these mediators, or to find ways to make the remaining neurons more tolerable to the hostile milieu crated by the ones that have already degenerated.

Our group discovered about four years ago that injured optic nerve or damaged retina deliver stress signal to the systemic immune system and recruit its help by leading to an evocation of T cell response directed against abundant antigens residing in the site of the stress. The immune response specificity is a way to bring T cells to the site of the lesion. Once activated, such T cells serve as a source of cytokines and neurotrophic factors affecting locally microglia, astrocytes and perhaps even neurons. In the course of our studies we realized that such an immune response is basically needed to help the body to cope with the injurious conditions and in disease conditions, like in trauma, need to be boosted (Moalem et al., 1999; Schori et al., 2001 and 2002; Kipnis et al., 2000).

We have discovered several ways that successfully boost the T cell-dependent immune response needed to protect damaged nerve from its hostile environment. A risk-free protection was found by the use of a compound that cross-reacts with a low affinity with a wide spectrum of self-antigens. One such compound is Copolymer 1 or glatiramer acetate. This compound has an enormous advantage that it is an approved drug for multiple sclerosis patients and thus does not carry the risk of causing an autoimmune disease (Schori et al., 2001 and 2002; Kipnis et al., 2000).

As described in our previous applications WO 01/52878 and WO 01/93893, Copolymer 1 emulsified in adjuvant was found to be protective for RGCs against elevated IOP in a chronic model of elevated IOP. Here we discovered that Cop-1 is strong enough and thus can evoke an intensive immune response that can protect effectively against consequences of IOP in both acute and chronic models of IOP. Interestingly, Cop-1, when administered in a regimen used for chronic MS disease, i.e. daily repeated injection, wipes out the benefit of a single injection, substantiating the contention that the requirements for autoimmune disease and for neurodegenerative disease are different (Schwartz and Kipnis, 2002; Kipnis and Schwartz, 2002). While the former needs suppression and the latter needs immune activation, the two may be met if one takes an approach of immunomodulation.

Another feature which became clear in the experiments of the present application is that intervention, in cases of RGC loss associated with chronic high IOP, is effective at any time in stopping disease progression. The fact that in the chronic model of IOP, interaction was more effective on day 7 than on day 0, do suggest that RGC loss is not initiated immediately after the pressure elevation, unlike in the acute model, in which the elevation of IOP is so high that death occurs much earlier.

That protection by vaccination with Cop-1 is not mediated by the drug Cop-1 itself, but by the immune response that it evokes, became evident when no effect was observed in T cell deprived animals. This explains why there is no need for daily administration of the drug for neuroprotection, as is often the case with pharmacological compounds that its clearance from the body is fast and there is a need for sustaining the drug. Administration of the compound, however, is needed periodically to sustain optimal level of T cells needed for the protection from the ongoing degeneration.

The way by which Cop-1 is protective in glaucoma is by evoking T cell response. The evoked T cells home to the eye in which they encounter microglia that can present the same self-antigen residing in the eye with which they can cross-react. The activated T cells are the source of cytokine and neurotrophic factors needed for the protection. Our in vitro studies have suggested that activated T cells can upregulate cluster of genes in microglia that can cope with stress and also genes that are associated with their buffering activity.

Other studies revealed that compound that can neutralize toxic compound in the eye could potentially be developed as a therapy for glaucoma. Among such compounds are NMDA antagonists, NO synthetase inhibitors. As glaucoma like any other neurodegenerative disease is not a single compound disease it is suggestive that in order to get a global protection one has to combine several drugs. The advantage of the vaccination according to the invention is in the fact that it simulates the body's own way of getting rid of stress and it invokes activity of the immune cells that is site-specific, but not insult-specific, and thus can protect from a wide range of threats.

According to the present invention, a single treatment with Cop 1 eye drops was found as an effective therapy in protecting RGCs against IOP-induced RGC loss in acute and chronic glaucoma rat models. In view of the previous publications by the inventors showing the neuroprotective effect of Cop 1 when injected to the animals, it was very surprising to discover that Cop 1 confers neuroprotection systemically when administered as eye drops.

In one preferred embodiment of the invention, the eye-drop vaccine comprising Copolymer 1, a Copolymer 1-related peptide or a Copolymer 1-related polypeptide is used to treat glaucoma, namely to arrest progression of glaucoma, a neurodegenerative disease of the optic nerve. As mentioned before, elevation of intraocular pressure (IOP) is often associated with chronic or acute glaucoma. However, very often, reduction of pressure is insufficient to stop disease progression. Elements of self-destruction are found to be associated with the disease progression. Here we show that a single vaccination with Cop 1, given in eye drops (or subcutaneously, for comparison) is sufficient to rescue RGCs from IOP-induced loss. Moreover, we found that in the chronic model of the disease, delayed treatment (7 days) is as effective as immediate treatment in the chronic model of IOP. Evidence is provided that treatment, either with the eye drops or systemically, is not directly effective but is immune-mediated. No effect is achieved in animals deprived of T cells, however the eye-drop effect is achieved when given contralaterally to the side with the elevated pressure in the eye. The results and route of immunization can be implemented immediately for clinical development.

According to the present invention, the preferred copolymer for use as the active agent of the invention is Cop 1, most preferably in the form of its acetate salt known under the generic name glatiramer acetate. The dosage of Cop 1 to be administered will be determined by the physician according to the age of the patient and stage of the disease and may be chosen from a range of 0.1 to 1,000 mg, preferably from a range of 10-80 mg, more preferably 20-60 mg, although any other suitable dosage is encompassed by the invention.

For multiple sclerosis patients, the administration may be made daily in one or more doses, preferably from one to three daily doses in a total of 0.1 to 1,000 mg, preferably within a range of 10-80 mg, more preferably 20-60 mg, or in alternate days, but any other suitable dosage is envisaged by the invention according to the condition of the patient. For non-multiple sclerosis patients, the dosage of Cop 1 is as indicated above in a periodical frequency, e.g. at least once a week, to at least once a month or at least once every 2 or 3 months, or less frequently, but any other suitable interval between the immunizations is envisaged by the invention according to the condition of the patient.

The following examples illustrate certain features of the present invention but are not intended to limit the scope of the present invention.

EXAMPLES

Materials and Methods (i) Animals.

Inbred adult male Lewis and Sprague-Dawley (SPD) rats (8 weeks; average weight 300 g) were supplied by the Animal Breeding Center at The Weizmann Institute of Science (Rehovot, Israel). The rats were maintained in a light- and temperature-controlled room and were matched for age and weight before each experiment. All animals were handled according to the regulations formulated by IACUC (International Animal Care and Use Committee).

(ii) Induction of Chronically High Intraocular Pressure (IOP).

Blockage of aqueous outflow causes an increase in IOP, which results in RGC death (Bakalash et al., 2002; Schori et al., 2001; Jia et al., 2000a; Levkovitch-Verbin et al., 2002). An increase in IOP was achieved in the right eyes of rats as follows. Rats were deeply anesthetized by intramuscular injection of ketamine hydrochloride (50 mg/kg) and xylazine hydrochloride (0.5 mg/kg). A slit lamp emitting blue-green argon laser irradiation (Haag-Streit, Köniz, Switzerland) was used to treat the right eye of the anesthetized rat with 80 to 120 applications directed toward three of the four episcleral veins and toward 270° of the limbal plexus. The laser beam was applied with a power of 1 W for 0.2 seconds, producing a spot size of 100 µm at the episcleral veins and 50 µm at the limbal plexus. At a second laser session 1 week later, the same parameters were used, except that the spot size was 100 µm in all applications. Irradiation was directed toward all four episcleral veins and 360° of the limbal plexus (Schori et al. 2001).

(iii) Induction of Acute High Intraocular Pressure.

An increase in IOP was achieved in the right eyes of deeply anesthetized rats (ketamine hydrochloride 50 mg/kg, xylazine hydrochloride 0.5 mg/kg, injected intramuscularly) by inserting a 30-gauge needle connected to a polyethylene tube and a bag of normal saline (0.9%) infusion. The infusion bag was placed 1 meter above the rat's head, creating a closed loop circulation. High IOP was induced for exactly 1 hour after which the needle was removed from the eye and the hole was self-sealed.

(iv) Measurement of Intraocular Pressure.

Most anesthetic agents cause a reduction in IOP (Jia et al., 2000b), thus precluding reliable measurement. To obtain accurate pressure measurements while the rat was in a tranquil state, we injected the rat intraperitoneally (i.p.) with 10 mg/mL acepromazine, a sedative drug that does not reduce IOP, and measured the pressure in both eyes 5 minutes later with a tonometer (Tono-Pen XL; Automated Ophthalmics, Ellicott City, Md., USA), after applying Localin to the cornea. Because of the reported effect of anesthetic drugs on IOP measured by Tono-Pen (Jia et al., 2000b), pressure was always measured at the same time after injection of acepromazine, and the average of 10 measurements taken from each eye was recorded. Measurements were taken on different occasions (every 2 days for 3 weeks), all at the same time of day. The untreated contralateral eye served as the control.

(v) Anatomical Assessment of Retinal Damage Caused by the Increase in IOP.

The hydrophilic neurotracer dye dextran tetramethylrhodamine (Rhodamine Dextran; (Molecular Probes, Eugene, Oreg., USA) was applied directly into the intraorbital portion of the optic nerve. Only axons that survive high IOP and remain functional with live cell bodies can take up the dye and demonstrate labeled RGCs. The rats were killed 24 hours later, and their retinas were excised, whole mounted, and preserved in 4% paraformaldehyde. The RGCs were counted under magnification of ×800 in a fluorescence microscope (Carl Zeiss, Oberkochen, Germany). From each retina four fields were counted, all with the same diameter (0.076 mm$^2$) and at the same distance from the optic disc (Kipnis et al., 2001; Yoles et al., 2001). Eyes from untreated rats were used as a control. RGCs were counted by an observer who was blinded to the identity of the retinas.

(vi) Active Immunization with Cop 1 and Adjuvant.

Rats with either laser-induced increase in IOP or acute IOP elevation were immunized with Cop 1 (100 µg) (Teva Pharmaceutical Industries Ltd., Petach Tikva, Israel) emulsified in 2.5 mg/ml of CFA in a total volume of 100 µl (Kipnis et al., 2000). Each animal was vaccinated subcutaneously at the root of the tail.

(vii) Active Immunization with Cop 1 and No Adjuvant.

Cop-1 in PBS was given at different concentrations and at different time points after the primary insult subcutaneously. Topical administration of Cop-1 was done after immersing the substance in PBS at a concentration of 20 mg/ml. Since each drop was of 50 µl, we administered 1 drop every 5 minutes for a total of 5 drops in 25 minutes.

Example 1

Cop-1 Vaccination Protects RGCs from IOP-Induced Death when Given without Vehicle Previous studies have shown that Cop 1 emulsified in an adjuvant protects against IOP-induced RGC death. Here we examined whether the effect is long-lasting in a chronic model.

Animals were subjected to unilateral elevation of IOP and immunized on the day of laser treatment (to induce IOP elevation). Rats were subjected to chronic elevation of IOP on the day of the first laser irradiation. Animals were divided into 4 groups: two groups received Cop-1 emulsified in CFA and two groups received PBS in CFA. From one group of Cop-1-treated animals retinas were excised 3 weeks later and the second group received Cop-1 2, 6 and 9 weeks latter. From this group, retinas were excised 12 weeks after the first laser irradiation. Of the two PBS-CFA-treated groups, one was analyzed for RGC survival 3 weeks after the first laser irradiation, and one received additional injection of PBS-CFA at 2, 6 and 9 weeks after the laser, and the retinas were excised 12 weeks after the first laser. The results are shown in FIG. 1. Assessment of the number of surviving RGCs 3 and 12 weeks later revealed a significant difference between the control and Cop-1 immunized and the PBS immunized rats, even 12 weeks following initiation of IOP elevation. Beneficial effect of Cop-1 (expressed as % of RGC death) was seen at 3 weeks (12.6±5 vs. 45.7±8, n=7) and at 12 weeks (33.7±1.4 vs. 57.2±6.3, n=5 and 4, respectively). Thus, 12 weeks after the first laser irradiation there was further loss of RGCs relative to 3 weeks (from 45.7% at 3 weeks to 57.20% by 12 weeks). Yet the vaccination reduced the loss at 12 weeks after the first laser to 33.7%. It seems that some loss was inevitable but some was amenable for protection even as long as 12 weeks after IOP was first elevated.

Example 2

Cop-1 Immunization without Adjuvant

Since Cop-1 is a high molecular weight compound with multiple epitopes, we considered the possibility that it might be immunogenic even without adjuvant.

Figure 2A:
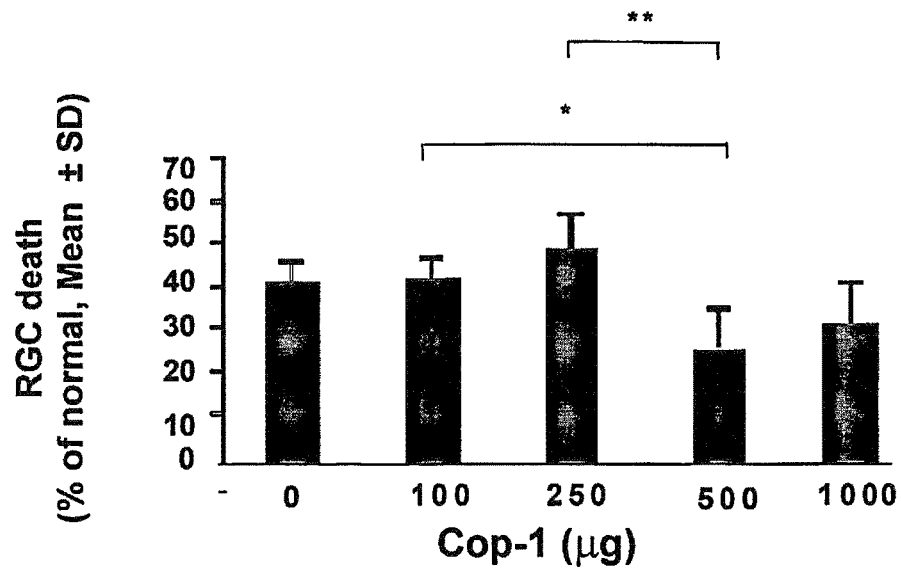
FIGS. 2A-2B show that immunization with 500 µg Cop-1 without adjuvant (2A) at the day 7 after the first laser (2B) protects RGCs from IOP-induced RGC death in a chronic model.

In a first experiment, rats were subjected to IOP elevation and received subcutaneous injection of different dosages of adjuvant-free Cop-1 at various dosages (100, 250, 500 and 1000 µg) on the first day of laser treatment; control animals received PBS. The results are depicted in FIG. 2A and show that the optimal effect could be achieved with 500 µg of Cop-1 injected subcutaneously to the rat; higher dosage or lower were less effective. The group treated with 500 µg showed the highest effect: 26.6±10% of RGC death as compared to 44±6% of RGC death in the group treated with 100 µg and 50.5±8% of RGC death in the group treated with 250 µg. In all groups 4-6 animals were included.

Figure 2B:
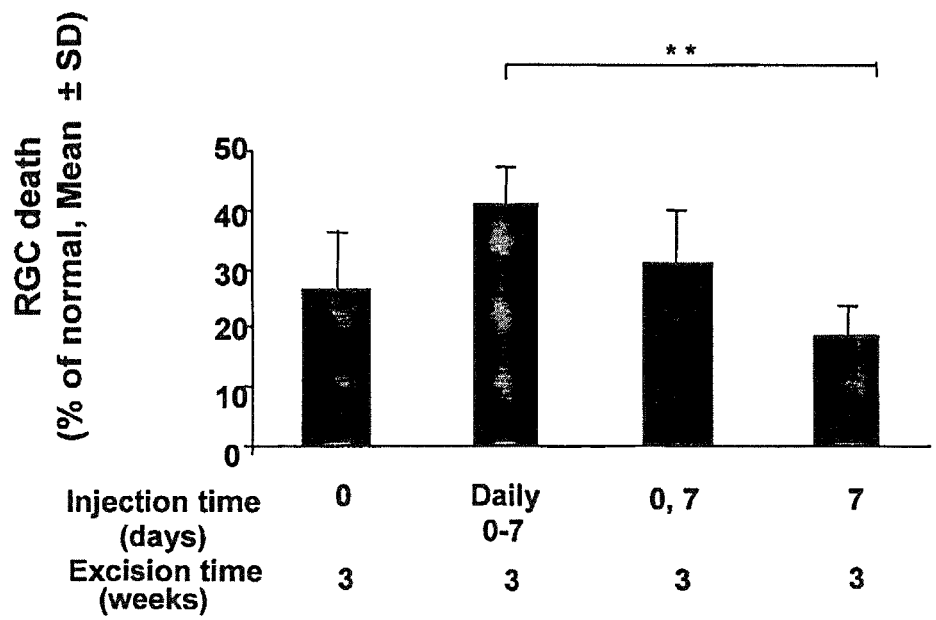

In another experiment, we also examined the timing and the frequency and found that injection on day 7 rather than on day 0 after IOP elevation was more effective, whereas repeated injection either at intervals of one week or daily, were less effective Rats were subjected to IOP and received 500 µg of adjuvant-free Cop-1 either immediately after the first laser (0), or a week later (7) or on both day 0 and day 7 (0, 7) or daily for 7 consecutive days starting on day 0 (0-7). The control group received PBS. Retinas were excised 3 weeks later. The results are depicted in FIG. 2B and show that the % of RGC death was lowest in the group that received a single injection on day 7 and highest in the group that received daily injections for 7 days (19.1±14.7 vs. 41.41±6, p<0.01).

The effect of adjuvant-free Cop-1 was also tested 6 weeks after IOP was first elevated. It was found that two injections—one on day 0 and the second one 3 weeks later—were more effective than a single injection after 3 weeks, suggesting that the vaccination should be synchronized with the kinetic of death, otherwise it is less effective. Since the death starts earlier than 3 weeks after IOP is first elevated, it is less effective if the first injection is given 3 weeks after IOP is first elevated.

Example 3

Cop-1 Effect is T-Cell Dependent

To verify that the effect of Cop-1 is indeed immune-mediated and does not act as a local drug, we administered Cop-1 to animals deprived of T cells in which IOP was elevated.

Figure 3A:
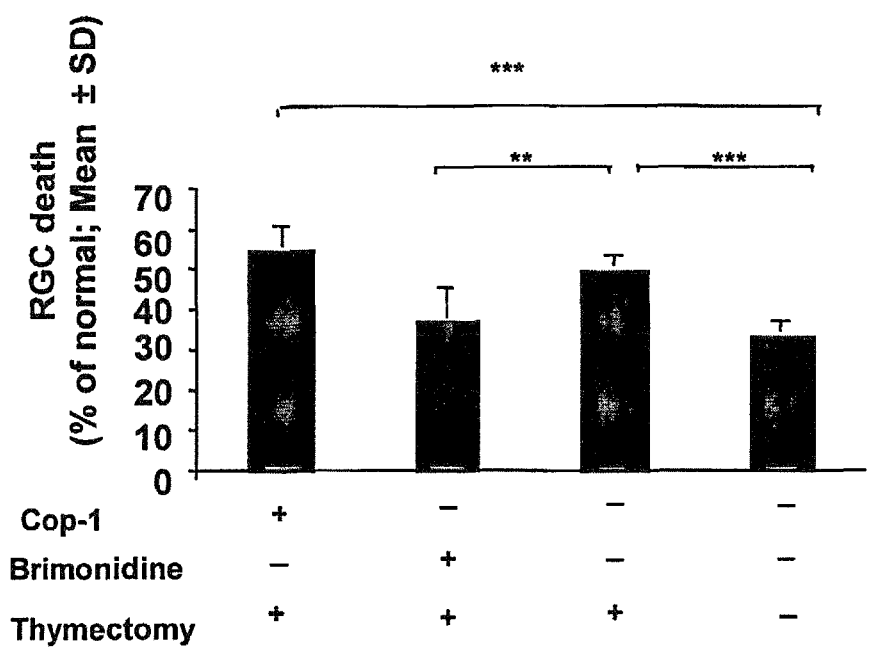
FIGS. 3A-3B show that the effect of Cop-1 is T cell-dependent. Treatment of elevated IOP in non-thymectomized animals with Cop-1 was more effective than in thymectomized animals (3A) and more effective than the glaucoma drug brimonidine (3B).
Figure 3B:
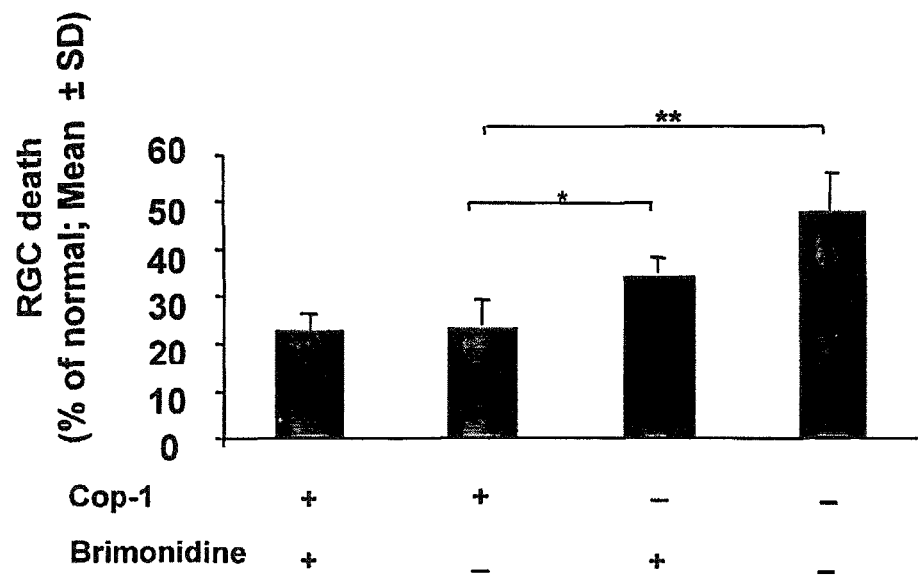

In a first experiment, normal adult rats and adult rats deprived of T cells (as a result of thymectomy at birth) were subjected to elevated IOP. Immediately after IOP elevation, animals received Cop-1, a single injection, or PBS, or daily brimonidine. Three weeks later retinae were excised and RGCs were counted. A lower percentage of RGCs died in non-thymectomized animals than in thymectomized animals following IOP elevation (34±3 vs. 50.2±3, $p<0.001$, n=6 and 5, respectively). As shown in FIGS. 3A and 3B, in the thymectomized animals treated with the $\alpha$2-adrenoreceptor agonist glaucoma drug brimonidine, the loss of RGCs was lower than in the non-treated thymectomized or in the Cop-1-treated thymectomized rats [38±7 (n=6) vs. 55±5.2 (n=5); p=0.001]. The effect of brimonidine and Cop-1 in non-thymectomized animals with elevated IOP is shown in FIG. 3B. Treatment in non-thymectomized animals with Cop-1 was more effective than brimonidine (23.5±5.7 vs. 34.5±3.51, $p<0.05$). The % of death in the control non-treated group was 47.9±7.5. No synergy between the two treatments was evident.

Thus, as expected, loss in T cell-deprived animals was higher than in normal animals (50% vs. 30%). Secondly, Cop-1 did not reduce IOP-induced RGC loss in T cell-deprived animals (55% vs. 50%). In contrast, the $\alpha$2-adrenoreceptor agonist used as a positive control, protected from RGC loss even in thymectomized animals (FIG. 3A). We also tested whether there is a synergy between the $\alpha$2-adrenoreceptor agonist brimonidine and Cop-1 in protecting RGCs from IOP-induced death in normal animals. FIG. 3B shows that there is no additive or synergy between the two compounds as far as the extent of RGC protection when given simultaneously. These results thus show that Cop-1 is a strong immunogen and can protect RGCs from IOP-induced death following a single injection 7 days after IOP is elevated.

Example 4

Cop-1 Eye Drops Protect RGCs in a Model of Chronic IOP

Figure 4A:
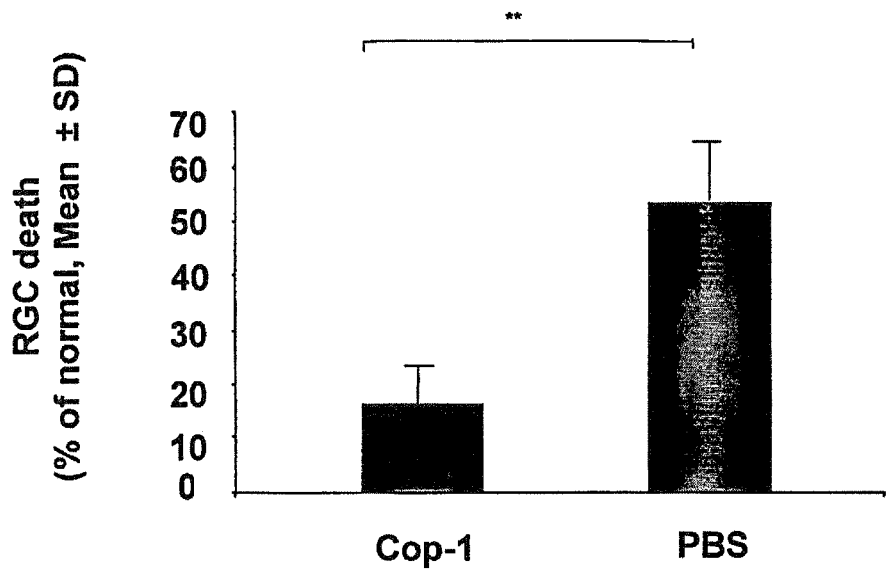
FIGS. 4A-4B show that Cop-1 applied in eye drops protects from IOP-induced RGC death in a chronic model. Five drops of 1 mg Cop-1 each given at 5-minute intervals were applied immediately (4A) or 7 days (4B) after IOP elevation in a chronic model of IOP elevation. Retinas were excised 3 weeks later.
Figure 4B:
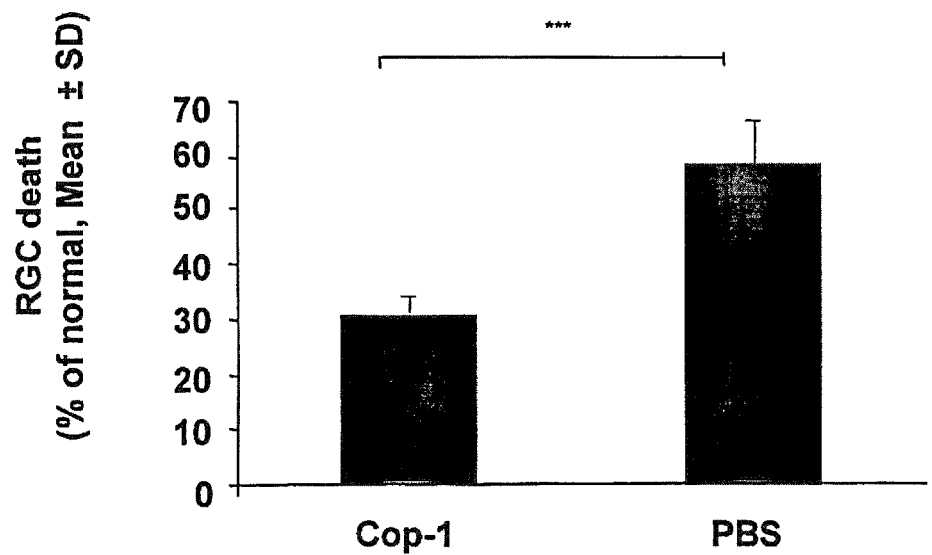

Since Cop-1 therapy is T cell-mediated and we have shown above that a single injection without adjuvant is sufficient to display protection, we explored now the possibility of using Cop-1 as eye drops without adjuvant. Assuming that approximately 10% of the eye drops get into the blood, we applied drops equivalent to 5 mg Cop-1 (ten-fold the optimal 500 μg found to be active when given subcutaneously). The Cop-1 eye drops were given either immediately (FIG. 4A) or 7 days (FIG. 4B) after IOP elevation in a chronic model. The Cop-1 protection with the eye drops was as effective as when given subcutaneously, when assessed 3 weeks after pressure elevation ($p<10^{-5}$; 103 RGCs vs. 150 RGCs).

Example 5

Cop-1 Eye Drops Protect RGCs from IOP-Induced Death in a Model of Acute IOP

The results of the chronic IOP encouraged us to examine whether Cop-1 can protect from IOP-induced loss of RGCs in an acute model of glaucoma.

We have previously established a well-calibrated model of a transient elevation of IOP (1 hour for 40 mm/Hg) which resulted 2 weeks later in an approximately 50% loss of RGCs. Application of Cop-1 without adjuvant in this acute model of IOP elevation resulted 2 weeks later in loss of only 20%.

Figure 5A:
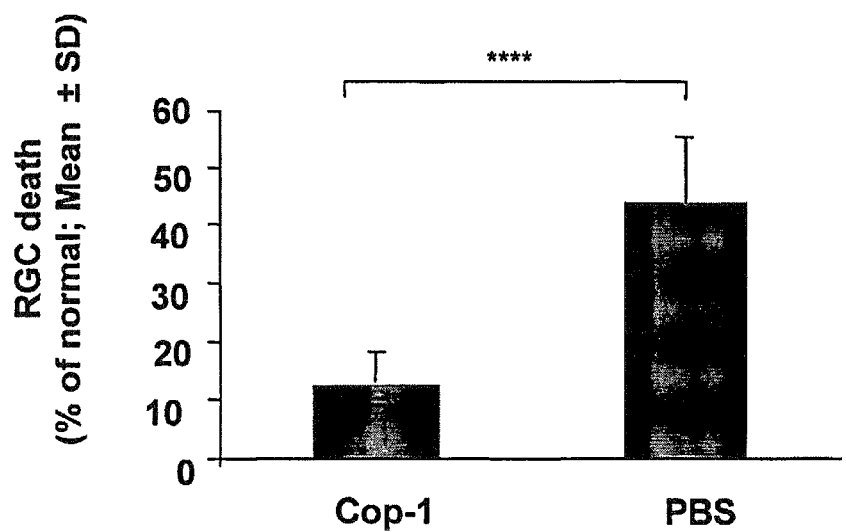
FIGS. 5A-5B show that Cop-1 protects RGCs against acute transient IOP elevation when administered subcutaneously (5A) or as eye drops (5B).
Figure 5B:
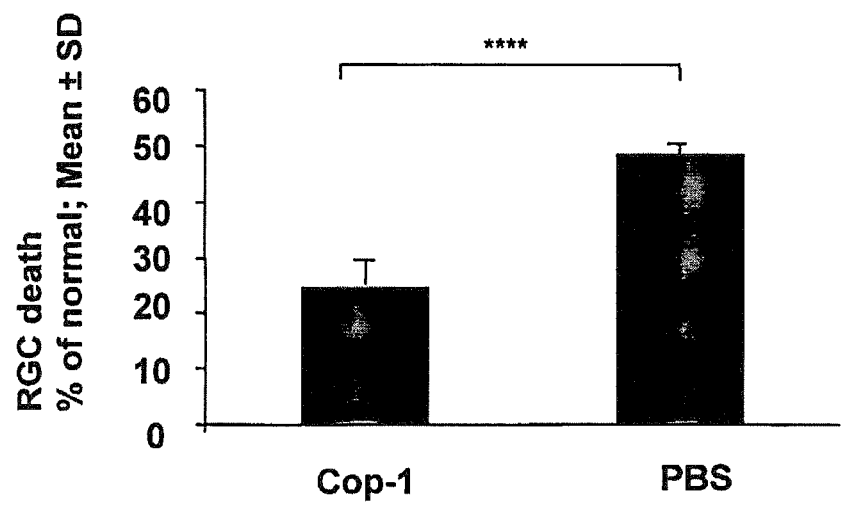

Using the acute IOP elevation model in Lewis rats with an average IOP of 54.75±11 mmHg, we vaccinated subcutaneously (FIG. 5A) or topically (eye drops; FIG. 5B) with either Cop-1 or vehicle (PBS). A total of 5 mg of Cop-1 was given to each animal during a course of 25 minutes immediately after an hour of elevated IOP. Average death rate two weeks after IOP elevation was 58.58%±7.42 (n=4) in the control group and 31.12%±3.22 in the Cop-1 vaccinated group (n=4) $p<0.001$).

It appeared that the two routes of administration were similarly effective in protecting RGCs, as assessed two weeks after the IOP was raised. To prove that the eye drops provide a route of immunization and not a way of local drug application, we elevated the pressure in one eye and applied Cop-1 in eye drops to the contralateral side. The same effect as when given ipsilaterally was obtained.

REFERENCES

Aharoni R., Teitelbaum D., Arnon R., Sela M. Copolymer 1 inhibits manifestation of graft rejection. *Transplantation* 27, 598 (2001)

Bakalash, S., Kipnis, J., Yoles, E. & Schwartz, M. Resistance of retinal ganglion cells to an increase in intraocular pressure is immune-dependent. *Invest. Ophthalmol. Vis. Sci.* 43, 2648-2653 (2002)

Fridkis-Hareli M, Neveu J M, Robinson R A, Lane W S, Gauthier L, Wucherpfennig K W, Sela M, Strominger J L. Binding motifs of copolymer 1 to multiple sclerosis- and rheumatoid arthritis-associated HLA-DR molecules. *J Immunol.* 162(8):4697-4704 (1999)

Fridkis-Hareli M, Santambrogio L, Stern J N, Fugger L, Brosnan C, Strominger J L. Novel synthetic amino acid copolymers that inhibit autoantigen-specific T cell responses and suppress experimental autoimmune encephalomyelitis. *J Clin Invest* 109(12):1635-1643 (2002)

Hauben, E., Nevo, U., Yoles, E., Moalem, G., Agranov, E., Mor, F., Akselrod, S., Neeman, M., Cohen, I. R., and Schwartz, M. Autoimmune T cells as potential neuroprotective therapy for spinal cord injury. *Lancet* 355:286-287 (2000)

Jia, L., Cepurna, W. O., Johnson, E. C. & Morrison, J. C. Patterns of intraocular pressure elevation after aqueous humor outflow obstruction in rats. *Invest. Ophthalmol. Vis. Sci.* 41, 1380-1385 (2000a)

Jia, L., Cepurna, W. O., Johnson, E. C. & Morrison, J. C. Effect of general anesthetics on IOP in rats with experimental aqueous outflow obstruction. *Invest. Ophthalmol. Vis. Sci.* 41, 3415-3419. (2000b)

Kipnis, J. & Schwartz, M. Dual Action of Glatiramer Acetate (Cop-1) as a Treatment for Autoimmune Diseases and a Vaccine for Protective Autoimmunity after CNS Injury. *Trends Mol. Med.* 8, 319-323 (2002)

Kipnis J, Yoles E, Porat Z, Cohen A, Mor F, Sela M, Cohen I R, Schwartz M. T cell immunity to copolymer 1 confers neuroprotection on the damaged optic nerve: possible therapy for optic neuropathies. *Proc. Natl. Acad. Sci. USA* 97, 7446-7451. (2000)

Kipnis J, Yoles E, Schori H, Hauben E, Shaked I, Schwartz M. Neuronal survival after CNS insult is determined by a genetically encoded autoimmune response. *J. Neurosci.* 21, 4564-4571. (2001)

Levkovitch-Verbin H, Quigley H A, Martin K R, Valenta D, Baumrind L A, Pease M E. Translimbal laser photocoagulation to the trabecular meshwork as a model of glaucoma in rats. *Invest. Ophthalmol. Vis. Sci.* 43, 402-410. (2002)

Mizrahi, T., Hauben, E. & Schwartz, M. The tissue-specific self-pathogen is the protective self-antigen: The case of uveitis. *J. Immunol.* 169, 5971-5977 (2002)

Moalem, G., Leibowitz-Amit R, Yoles E, Mor F, Cohen I R, Schwartz M. Autoimmune T cells protect neurons from secondary degeneration after central nervous system axotomy. *Nat. Med.* 5, 49-55 (1999)

Mukibi-Muka G, Jones R C, Kibenge F S. Serological response and virus shedding of chickens inoculated with reovirus via different routes. *Res Vet Sci* 37(2):227-9 (1984)

Russell P H, Mackie A. Eye-drop DNA can induce IgA in the tears and bile of chickens. *Vet Immunol Immunopathol* 80(3-4):327-32 (2001)

Schlegel P G, Aharoni R, et al. A synthetic random copolymer with promiscuous binding to class II MHC molecules inhibits T-cell proliferative response to major and minor histocompatibility antigens in vitro and confers the capacity to prevent murine graft-versus-host disease in vivo. *Proc. Natl. Acad. Sci. USA.* 93, 5061 (1996)

Schori, H., J. Kipnis, E. Yoles, E. WoldeMussie, G. Ruiz, L. A. Wheeler, and M. Schwartz. Vaccination for protection of retinal ganglion cells against death from glutamate cytotoxicity and ocular hypertension: implications for glaucoma. *Proc. Natl. Acad. Sci. USA* 98, 3398-3403. (2001)

Schori, H., Lantner, F., Shachar, I. & Schwartz, M. Severe immunodeficiency has opposite effects on neuronal survival in glutamate-susceptible and -resistant mice: Adverse effect of B cells. *J. Immunol.* 169, 2861-2865 (2002)

Schwartz, M., Belkin, M., Yoles, E. & Solomon, A. Potential treatment modalities for glaucomatous neuropathy: neuroprotection and neuroregeneration. *J. Glaucoma* 5, 427-432 (1996)

Schwartz, M. & Kipnis, J. Multiple sclerosis as a by-product of the failure to sustain protective autoimmunity: A paradigm shift. *The Neuroscientist* 8, 405-413 (2002)

Schwartz, M. & Yoles, E. Neuroprotection: a new treatment modality for glaucoma? *Curr. Opin. Ophthalmol.* 11, 107-111 (2000a)

Schwartz, M. & Yoles, E. Self-destructive and self-protective processes in the damaged optic nerve: implications for glaucoma. *Invest. Ophthalmol. Vis. Sci.* 41, 349-351 (2000b)

Sharma J M. Introduction to poultry vaccines and immunity. *Adv. Vet. Med.* 41, 481-94 (1999)

Yoles E, Hauben E, Palgi O, Agranov E, Gothilf A, Cohen A, Kuchroo V, Cohen I R, Weiner H, Schwartz M. Protective autoimmunity is a physiological response to CNS trauma. *J. Neurosci.* 21, 3740-3748. (2001)

---

The invention claimed is:

1. A method of therapeutic immunization of a glaucoma patient, which comprises topically administering to the eye of the patient an eye-drop vaccine comprising Copolymer 1 in an amount effective to confer systemic neuroprotection by evoking an immune response and thereby to treat glaucoma in said patient.

2. A method for reducing neuronal degeneration caused by the neurodegenerative effects of a disease, or for reducing secondary neuronal degeneration that follows the primary neuronal degeneration of an injury, in the central nervous system (CNS) or peripheral nervous system (PNS) of an individual in need thereof, which method comprises immunizing the individual in need by topically administering an eye-drop vaccine to the eye of the individual, said vaccine comprising an active agent comprising Copolymer 1, in an amount effective to confer systemic neuroprotection by evoking an immune response and thereby to reduce said neuronal degeneration caused by injury or disease in said individual.

3. A method of therapeutic immunization comprising immunizing a human individual in need with an eye-drop vaccine, which comprises an active agent comprising Copolymer 1, wherein said immunizing comprises administering said vaccine to the eye of the individual in an amount effective to confer systemic neuroprotection by evoking an immune response and thereby therapeutic immunization of said human individual.

4. The method of therapeutic immunization according to claim 3, for treating neuronal degeneration caused by an injury, disease, disorder or condition in the central nervous system (CNS) or peripheral nervous system (PNS), for preventing or inhibiting neuronal secondary degeneration which may otherwise follow a primary injury in the CNS, which method comprises immunizing a human individual in need with an eye-drop vaccine comprising Copolymer 1, in an amount effective to confer systemic neuroprotection and thereby to treat, prevent or inhibit said neuronal degeneration caused by said injury, disease, disorder or condition in the human individual.

5. The method according to claim 4, wherein said disease is multiple sclerosis.

6. The method according to claim 5, wherein said vaccine is administered at a frequency of at least once every day or every alternate day to a multiple sclerosis patient.

7. The method according to claim 4, which comprises immunization with the active agent without an adjuvant.

8. The method according to claim 4, which comprises immunization with the active agent with a soluble adjuvant.

9. The method according to claim 4, wherein said vaccine is administered periodically at a frequency selected from the group consisting of at least once every seven days, at least once every month, and at least once every 2-3 months, to a non-multiple sclerosis patient.

10. The method according to claim 4, wherein said injury is spinal cord injury, blunt trauma, penetrating trauma, brain coup or contrecoup, hemorrhagic stroke, or ischemic stroke.

11. The method according to claim 4, wherein said disease is glaucoma.

12. The method of claim 3 in which a T-cell response is evoked.

13. The method of claim 12 in which the T-cell response comprises activation of T-cells, and the activated T-cells produce one or more neuroprotective cytokines or neurotrophic factors.

14. The method of claim 13 in which the activated T cells interact with microglia in the eye.

* * * * *